United States Patent
Goutsis et al.

(10) Patent No.: US 10,441,521 B2
(45) Date of Patent: Oct. 15, 2019

(54) METHOD FOR STRAIGHTENING, CONDITIONING AND COLOURING HAIR, ESPECIALLY HAIR WITH SUBSTANTIAL CURL

(71) Applicant: Henkel AG & Co. KGaA, Duesseldorf (DE)

(72) Inventors: Konstantin Goutsis, Juechen (DE); Gabriele Weser, Neuss (DE)

(73) Assignee: Henkel AG & Co. KGaA (DE)

( * ) Notice: Subject to any disclaimer, the term of this patent is extended or adjusted under 35 U.S.C. 154(b) by 117 days.

(21) Appl. No.: 15/175,831

(22) Filed: Jun. 7, 2016

(65) Prior Publication Data

US 2016/0287502 A1    Oct. 6, 2016

Related U.S. Application Data

(63) Continuation of application No. PCT/EP2014/075139, filed on Nov. 20, 2014.

(30) Foreign Application Priority Data

Dec. 12, 2013 (DE) .......................... 10 2013 225 788

(51) Int. Cl.
*A61K 8/46* (2006.01)
*A61K 8/43* (2006.01)
*A61Q 5/04* (2006.01)
*A61Q 5/06* (2006.01)
*A61Q 5/12* (2006.01)
*A61K 8/19* (2006.01)
*A61K 8/23* (2006.01)
*A45D 7/04* (2006.01)
*A61K 8/81* (2006.01)
*A45D 7/00* (2006.01)

(52) U.S. Cl.
CPC ............... *A61K 8/466* (2013.01); *A45D 7/04* (2013.01); *A61K 8/19* (2013.01); *A61K 8/23* (2013.01); *A61K 8/43* (2013.01); *A61K 8/46* (2013.01); *A61K 8/8152* (2013.01); *A61Q 5/04* (2013.01); *A61Q 5/065* (2013.01); *A61Q 5/12* (2013.01); *A45D 2007/001* (2013.01); *A61K 2800/432* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 3,399,682 A | * | 9/1968 | Isaji | A61K 8/46 132/204 |
| 3,971,391 A | * | 7/1976 | Bore | A61Q 5/04 132/202 |
| 4,963,349 A | * | 10/1990 | Mathews | A61K 8/345 424/70.5 |
| 5,904,919 A | * | 5/1999 | Brautigam | A61K 8/46 424/70.122 |
| 6,058,943 A | * | 5/2000 | Davis-Harris | A45D 7/04 132/205 |
| 2005/0076459 A1 | | 4/2005 | Guardia, Jr. et al. | |

FOREIGN PATENT DOCUMENTS

| | | | | |
|---|---|---|---|---|
| FR | 2931667 A1 | | 4/2009 | |
| JP | 2003-231619 A | | 8/2003 | |
| JP | 2009173574 A | * | 8/2009 | |
| WO | WO-2010000582 A2 | * | 1/2010 | ............. A61K 8/416 |
| WO | 2013/098335 A2 | | 7/2013 | |

OTHER PUBLICATIONS

Machine translation, JP 2009-173574, printed 2018.*
Taketombo "Red No. 2," printed 2018; http://www.taketombo.co.jp/ci/r2e.htm.*
Machine translation WO 2010/000582, printed 2018.*
PCT International Search Report (PCT/EP2014/075139) dated Feb. 26, 2015.

* cited by examiner

Primary Examiner — Bong-Sook Baek
(74) Attorney, Agent, or Firm — James J. Cummings

(57) ABSTRACT

A method for straightening and dyeing keratinous fibers includes the following steps: A) treating the fibers with a straightening agent (G), B) treating the fibers with a conditioner (K), and C) treating the fibers with a coloring agent (F). The straightening composition (G) includes at least one alkalizing agent selected from sodium hydroxide, potassium hydroxide, lithium hydroxide, magnesium hydroxide, calcium hydroxide, and/or guanidinium hydroxide, the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or cosmetically acceptable salts thereof, and the coloring agent (F) includes at least one direct acid dye.

16 Claims, No Drawings

METHOD FOR STRAIGHTENING, CONDITIONING AND COLOURING HAIR, ESPECIALLY HAIR WITH SUBSTANTIAL CURL

FIELD OF THE INVENTION

The present invention generally relates a method for treating hair, in particular very curly hair, which allows the hair to be straightened, conditioned, and dyed. A further subject matter of the present invention relates to a multi-component packaging unit (kit) that includes a straightening agent, a conditioner, and a coloring agent which are separately packaged. The coloring agent includes at least one direct acid dye, and the conditioner and/or the coloring agent include(s) at least one reducing agent.

BACKGROUND OF THE INVENTION

Changing the shape and color of keratinous fibers, in particular hair, represents an important area of modern cosmetics. The appearance of the hair may thus be adapted to current fashion trends and to the person's individual preferences. Coloring, in particular covering up gray hair, is sought by people of all cultures. People from cultures with naturally curly hair also often seek options for straightening the hair.

Hair straightening agents are used for straightening curly hair. In this regard, the hair straightening agents must meet a number of minimum requirements: The agents must allow effective straightening of the very curly hair, in particular for the very strong curl found in African type hair, for example, wherein the straightening should take place regardless of the condition of the hair. In addition, the agents must have temperature stability, should have an optimal consistency, should not cause skin irritation, and should be capable of being easily washed out. Furthermore, the agents should not cause excessive damage to the hair. The most commonly used method of straightening very curly hair is treatment of the hair with preparations based on sodium hydroxide, potassium hydroxide, lithium hydroxide, and/or guanidinium hydroxide. When these hair straightening agents are applied, the cystine bonds present in the hair are cleaved, and approximately one-third of the cystine is converted to lanthionine. Since the hair straightening carried out using the above-mentioned hydroxides exposes the hair to strong alkalinity, damage to the hair is often not avoidable.

For changing the color of the hair, those skilled in the art are familiar with various coloring systems, depending on the requirements for the coloring. For long-lasting, intense colorations having appropriate fastness properties, so-called oxidation dyes are used. Such coloring agents customarily include oxidation dye precursors, so-called developer components and coupler components, which form the actual dyes with one another under the influence of oxidizing agents, for example hydrogen peroxide. Oxidation dyes are characterized by excellent, long-lasting color results, but are also associated with a certain degree of damage to the hair. When oxidation dyes are used in combined straightening-dyeing processes, the damage would accumulate, for which reason the use of oxidation dyes in straightening-dyeing processes is not indicated.

The hair color may be temporarily changed by using direct dyes. In the process, dyes which are already formed diffuse from the coloring agent into the hair fiber. Compared to oxidative hair coloring, the colorings obtained with direct dyes are not as durable and wash out more quickly. However, the lesser amount of damage from coloring with direct dyes is advantageous.

Methods for combined straightening and dyeing of hair have already been described in the prior art. For example, WO 2013/098335 A2 discloses a method for straightening and dyeing keratin fibers, in which hydroxide bases and dyes are simultaneously applied to the fibers. However, the methods and agents known from the prior art are often associated with a high to a very high level of damage to the hair.

It is therefore desirable to provide a low-damage method for straightening and dyeing keratinous fibers. By use of this method, the aim in particular is to allow even very curly hair, such as African type hair, for example, to be effectively straightened and dyed. The hair should preferably experience less damage due to this method.

Furthermore, other desirable features and characteristics of the present invention will become apparent from the subsequent detailed description of the invention and the appended claims, taken in conjunction with this background of the invention.

BRIEF SUMMARY OF THE INVENTION

A method for straightening and dyeing keratinous fibers includes the following steps: A) treating the fibers with a straightening agent (G), B) treating the fibers with a conditioner (K), and C) treating the fibers with a coloring agent (F). The straightening agent (G) includes at least one alkalizing agent selected from sodium hydroxide, potassium hydroxide, lithium hydroxide, magnesium hydroxide, calcium hydroxide, and/or guanidinium hydroxide; the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof; and the coloring agent (F) includes at least one direct acid dye.

A multicomponent packaging unit (kit) includes three separately packaged cosmetic agents (G), (K), and (F). The straightening agent (G) includes at least one alkalizing agent selected from sodium hydroxide, potassium hydroxide, lithium hydroxide, magnesium hydroxide, calcium hydroxide, and/or guanidinium hydroxide; the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof; and the coloring agent (F) includes at least one direct acid dye.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that keratinous fibers having a strong curl may be effectively straightened and intensely dyed when they are subjected to a specific method which includes alkaline straightening, conditioning of the fibers, and coloring with acid dyes. The damage to the hair may surprisingly be minimized to a particularly high degree when the conditioner and/or the coloring agent include(s) a reducing agent.

A first aspect of the present invention relates to a method for straightening and dyeing keratinous fibers, including the following steps:
A) treating the fibers with a straightening agent (G),
B) treating the fibers with a conditioner (K),
C) treating the fibers with a coloring agent (F),
wherein
  the straightening agent (G) includes at least one alkalizing agent selected from sodium hydroxide, potassium hydroxide, lithium hydroxide, magnesium hydroxide, calcium hydroxide, and/or guanidinium hydroxide,
  the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof, and
  the coloring agent (F) includes at least one direct acid dye.

Keratinous fibers, keratin-containing fibers, or keratin fibers are understood to mean fur, wool, feathers, and in particular human hair. Although the agents according to the invention are primarily suited for lightening and dyeing keratin fibers, use in other fields is also possible in principle.

The use of straightening agent (G), conditioner (K), and coloring agent (F) is characterizing for the method according to the invention. These three agents involve three different cosmetic agents which each include all essential ingredients in a cosmetic carrier. The cosmetic carrier may be a suitable aqueous, alcoholic, or aqueous-alcoholic carrier. For example, the straightening agent (G), the conditioner (K), and the coloring agent (F) may in each case be applied to the keratinous fibers in the form of a cream, an emulsion, a gel, or also in the form of a surfactant-containing foaming solution such as a shampoo, a foam aerosol, a foam formulation, or in the form of some other preparation that is suitable for application to the hair.

In the method according to the invention, the straightening agent (G) is applied first, after which the conditioner (K) and the coloring agent (F) may be applied.

In the first case, a method according to the invention comprises the following steps in the stated sequence:
A) treating the fibers with a straightening agent (G),
B) treating the fibers with a conditioner (K),
C) treating the fibers with a coloring agent (F).

In the second case, a method according to the invention comprises the following steps in the stated sequence:
A) treating the fibers with a straightening agent (G),
C) treating the fibers with a coloring agent (F),
B) treating the fibers with a conditioner (K).

Both embodiment types of the method allow the straightening and dyeing of the keratinous fibers with very little damage.

A first particularly preferred embodiment is therefore a method for straightening and dyeing keratinous fibers, including the following steps in the stated sequence:
A) treating the fibers with a straightening agent (G),
B) treating the fibers with a conditioner (K),
C) treating the fibers with a coloring agent (F),
wherein
  the straightening agent (G) includes at least one alkalizing agent selected from sodium hydroxide, potassium hydroxide, lithium hydroxide, magnesium hydroxide, calcium hydroxide, and/or guanidinium hydroxide,
  the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof, and
  the coloring agent (F) includes at least one direct acid dye.

A second particularly preferred embodiment is a method for straightening and dyeing keratinous fibers, including the following steps in the stated sequence:
A) treating the fibers with a straightening agent (G),
C) treating the fibers with a coloring agent (F),
B) treating the fibers with a conditioner (K),
wherein
  the straightening agent (G) includes at least one alkalizing agent selected from sodium hydroxide, potassium hydroxide, lithium hydroxide, magnesium hydroxide, calcium hydroxide, and/or guanidinium hydroxide,
  the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof, and
  the coloring agent (F) includes at least one direct acid dye.

In the first step (A) of the first embodiment of the method according to the invention, a cosmetic straightening agent (G) is applied to the fibers. The straightening agent (G) is preferably allowed to act on the keratin fibers for a period of 30 seconds to 45 minutes, after which it is rinsed out. In one embodiment, the keratin fibers are subsequently treated with the conditioner (K) (i.e., in second step (B)). The conditioner (K) is preferably allowed to act on the keratin fibers for a period of 30 seconds to 45 minutes before it is rinsed out. Rinsing out of the conditioner is followed (in third step (C)) by the coloring with a coloring agent (F) which includes at least one acid dye. The coloring agent (F) is preferably allowed to act for a period of 30 seconds to 45 minutes before it is rinsed out.

The straightening of the keratin fibers may be carried out while the straightening agent (G) is acting on the keratin fibers or shortly after the straightening agent (G) is washed out. In this regard, the straightening preferably takes place mechanically, for example by drawing it out with a comb or a brush. The straightening may also be carried out with the aid of a straightening iron, although the associated effect from heat may additionally damage the keratin fibers.

Another preferred embodiment is therefore a method for straightening and dyeing keratinous fibers, including the following steps in the stated sequence:
A) treating the fibers with a straightening agent (G),
B) treating the fibers with a conditioner (K),
C) treating the fibers with a coloring agent (F),
wherein
  the straightening agent (G) includes at least one alkalizing agent selected from sodium hydroxide, potassium hydroxide, lithium hydroxide, magnesium hydroxide, calcium hydroxide, and/or guanidinium hydroxide,
  the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof,
  the coloring agent (F) includes at least one direct acid dye, and
  the straightening of the keratin fibers takes place mechanically in step A) or directly after step A).

A second particularly preferred embodiment is a method for straightening and dyeing keratinous fibers, including the following steps in the stated sequence:
A) treating the fibers with a straightening agent (G),
C) treating the fibers with a coloring agent (F),
B) treating the fibers with a conditioner (K),
wherein
- the straightening agent (G) includes at least one alkalizing agent selected from sodium hydroxide, potassium hydroxide, lithium hydroxide, magnesium hydroxide, calcium hydroxide, and/or guanidinium hydroxide,
- the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof,
- the coloring agent (F) includes at least one direct acid dye, and
- the straightening of the keratin fibers takes place in step A) or directly after step A).

When the straightening is carried out in step A), this means that the straightening takes place while the straightening agent (G) is present on the keratin fibers. If the straightening takes place directly after step A), the straightening is carried out after the straightening agent (G) is rinsed out and before the next agent according to the method is applied (i.e., before the conditioner (K) and/or the coloring agent (F) are/is applied).

In principle, the period of time between washing out the straightening agent (G) and applying the conditioner (K) may be up to 48 hours. However, it is preferred when there is a period of 24 hours maximum, even more preferably 12 hours maximum, and particularly preferably 30 minutes maximum, between these two steps.

Likewise, the period of time between washing out the conditioner (K) and applying the coloring agent (F) may be up to 48 hours. However, it is preferred when there is a period of 24 hours maximum, even more preferably 12 hours maximum, and particularly preferably 30 minutes maximum, between these two steps.

Therefore, a method of the first subject matter of the invention is very particularly preferred which comprises the following steps in the stated sequence:
A1) applying a straightening agent (G) to the fibers,
A2) allowing the straightening agent (G) to act for a period of 30 seconds to 45 minutes,
A3) rinsing out the straightening agent (G),
B1) applying a conditioner (K) to the fibers,
B2) allowing the conditioner (K) to act for a period of 30 seconds to 45 minutes,
B3) rinsing out the conditioner (K),
C1) applying a coloring agent (F) to the fibers,
C2) allowing the coloring agent to act for a period of 30 seconds to 45 minutes,
C3) rinsing out the coloring agent (F),
wherein
- there is a time interval of 10 seconds to 48 hours, preferably 10 seconds to 24 hours, more preferably 10 seconds to 12 hours, and particularly preferably 10 seconds to 30 minutes, between steps A3) and B1) and
- there is a time interval of 10 seconds to 48 hours, preferably 10 seconds to 24 hours, more preferably 10 seconds to 12 hours, and particularly preferably 10 seconds to 30 minutes, between steps B3) and C1).

A method is also preferred which comprises the following steps in the stated sequence:
A1) applying a straightening agent (G) to the fibers,
A2) allowing the straightening agent (G) to act for a period of 30 seconds to 45 minutes,
A3) rinsing out the straightening agent (G),
B1) applying a conditioner (K) to the fibers,
B2) allowing the conditioner (K) to act for a period of 30 seconds to 45 minutes,
B3) rinsing out the conditioner (K),
C1) applying a coloring agent (F) to the fibers,
C2) allowing the coloring agent to act for a period of 30 seconds to 45 minutes,
C3) rinsing out the coloring agent (F),
wherein
- there is a time interval of 10 seconds to 30 minutes between steps A3) and B1) and
- there is a time interval of 10 seconds to 30 minutes between steps B3) and C1).

A method is also preferred which comprises the following steps in the stated sequence:
A1) applying a straightening agent (G) to the fibers,
A2) allowing the straightening agent (G) to act for a period of 30 seconds to 45 minutes,
A3) rinsing out the straightening agent (G),
B1) applying a conditioner (K) to the fibers,
B2) allowing the conditioner (K) to act for a period of 30 seconds to 45 minutes,
B3) rinsing out the conditioner (K),
C1) applying a coloring agent (F) to the fibers,
C2) allowing the coloring agent to act for a period of 30 seconds to 45 minutes,
C3) rinsing out the coloring agent (F),
wherein
- there is a time interval of 10 seconds to 30 minutes between steps A3) and B1) and
- there is a time interval of 10 seconds to 30 minutes between steps B3) and C1).

Within the scope of the second particularly preferred embodiment of the method according to the invention, a cosmetic straightening agent (G) is applied to the fibers in first step (A). The straightening agent (G) is preferably allowed to act on the keratin fibers for a period of 30 seconds to 45 minutes, after which it is rinsed out. Within this embodiment, the keratin fibers are subsequently treated with the coloring agent (F) (i.e., in second step (C)). The coloring agent (F) is preferably allowed to act on the keratin fibers for a period of 30 seconds to 45 minutes before it is rinsed out. Rinsing out of the coloring agent is followed (in third step (B)) by application of the conditioner (K). The conditioner (K) is preferably allowed to act for a period of 30 seconds to 45 minutes before it is rinsed out.

In principle, the period of time between washing out the straightening agent (G) and applying the coloring agent (F) may be up to 48 hours. However, it is preferred when there is a period of 24 hours maximum, even more preferably 12 hours maximum, and particularly preferably 30 minutes maximum, between these two steps.

Likewise, in principle the period of time between washing out the coloring agent (F) and applying the conditioner (K) may be up to 48 hours. However, it is preferred when there is a period of 24 hours maximum, even more preferably 12 hours maximum, and particularly preferably 30 minutes maximum, between these two steps.

Therefore, a method of the first subject matter of the invention is very particularly preferred which comprises the following steps in the stated sequence:
A1) applying a straightening agent (G) to the fibers,
A2) allowing the straightening agent (G) to act for a period of 30 seconds to 45 minutes,
A3) rinsing out the straightening agent (G),
C1) applying a coloring agent (F) to the fibers,
C2) allowing the coloring agent to act for a period of 30 seconds to 45 minutes,
C3) rinsing out the coloring agent (F),
B1) applying a coloring agent (F) to the fibers,
B2) allowing the coloring agent to act for a period of 30 seconds to 45 minutes,
B3) rinsing out the coloring agent (F),
wherein
there is a time interval of 10 seconds to 48 hours, preferably 10 seconds to 24 hours, more preferably 10 seconds to 12 hours, particularly preferably 10 seconds to 30 minutes, between steps A3) and C1) and
there is a time interval of 10 seconds to 48 hours, preferably 10 seconds to 24 hours, more preferably 10 seconds to 12 hours, particularly preferably 10 seconds to 30 minutes. between steps C3) and B1).

Therefore, a method of the first subject matter of the invention is also very particularly preferred which comprises the following steps in the stated sequence:
A1) applying a straightening agent (G) to the fibers,
A2) allowing the straightening agent (G) to act for a period of 30 seconds to 45 minutes,
A3) rinsing out the straightening agent (G),
C1) applying a coloring agent (F) to the fibers,
C2) allowing the coloring agent to act for a period of 30 seconds to 45 minutes,
C3) rinsing out the coloring agent (F),
B1) applying a conditioner (K) to the fibers,
B2) allowing the conditioner (K) to act for a period of 30 seconds to 45 minutes,
B3) rinsing out the conditioner (K),
wherein
there is a time interval of 10 seconds to 30 minutes between steps A3) and C1) and
there is a time interval of 10 seconds to 30 minutes between steps C3) and B1).

Therefore, a method of the first subject matter of the invention is also very particularly preferred which comprises the following steps in the stated sequence:
A1) applying a straightening agent (G) to the fibers,
A2) allowing the straightening agent (G) to act for a period of 30 seconds to 45 minutes,
A3) rinsing out the straightening agent (G),
C1) applying a coloring agent (F) to the fibers,
C2) allowing the coloring agent to act for a period of 30 seconds to 45 minutes,
C3) rinsing out the coloring agent (F),
B1) applying a conditioner (K) to the fibers,
B2) allowing the conditioner (K) to act for a period of 30 seconds to 45 minutes,
B3) rinsing out the conditioner (K),
wherein
there is a time interval of 10 seconds to 30 minutes between steps A3) and C1),
there is a time interval of 10 seconds to 30 minutes between steps C3) and B1), and
the straightening of the keratin fibers takes place in step A) or directly after step A).

The minimum time interval of 10 seconds represents the minimum amount of time required by the user, after washing out of the previously applied agent is completed, for taking the next agent, emptying it from the container in which it is provided, and applying it to the keratin fibers.

A feature of the method for straightening and dyeing the keratinous fibers which is essential to the invention is that the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof. Accordingly, either only the conditioner (K) can include at least one reducing agent from the above-mentioned group, or only the coloring agent (F) can include at least one reducing agent from the above-mentioned group, or the conditioner (K) and the coloring agent (F) both include at least one reducing agent from the above-mentioned group.

Therefore, a method for straightening and dyeing keratinous fibers is also preferred which comprises the following steps:
A) treating the fibers with a straightening agent (G),
B) treating the fibers with a conditioner (K),
C) treating the fibers with a coloring agent (F),
wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the conditioner (K) includes at least one reducing agent selected from thiolactic acid, thioglycolic acid, cysteine, sodium sulfide, sodium sulfite, sodium thiosulfate, sodium dithionite, and/or the cosmetically acceptable salts thereof, and
the coloring agent (F) includes at least one direct acid dye.

A method for straightening and dyeing keratinous fibers is likewise preferred which comprises the following steps:
A) treating the fibers with a straightening agent (G),
B) treating the fibers with a conditioner (K),
C) treating the fibers with a coloring agent (F),
wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the coloring agent (F) includes at least one reducing agent selected from thiolactic acid, thioglycolic acid, cysteine, sodium sulfide, sodium sulfite, sodium thiosulfate, sodium dithionite, and/or the cosmetically acceptable salts thereof, and
the coloring agent (F) includes at least one direct acid dye.

A method for straightening and dyeing keratinous fibers is also preferred which comprises the following steps:
A) treating the fibers with a straightening agent (G),
B) treating the fibers with a conditioner (K),
C) treating the fibers with a coloring agent (F),
wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the conditioner (K) and the coloring agent (F), independently of one another, each include at least one reducing agent selected from thiolactic acid, thioglycolic acid, cysteine, sodium sulfide, sodium sulfite, sodium thiosulfate, sodium dithionite, and/or the cosmetically acceptable salts thereof, and the coloring agent (F) includes at least one direct acid dye.

For using the method according to the invention, it is particularly convenient for the user and therefore preferred when the user successively applies the agents which are provided in the form of a multicomponent packaging unit (i.e., in the form of a kit).

A second subject matter of the present invention therefore relates to a multicomponent packaging unit (kit) which comprises three separately packaged cosmetic agents (G), (K), and (F), wherein
- the straightening agent (G) includes at least one alkalizing agent selected from sodium hydroxide, potassium hydroxide, lithium hydroxide, magnesium hydroxide, calcium hydroxide, and/or guanidinium hydroxide,
- the conditioner (K) and/or the coloring agent (F) include(s) at least one reducing agent selected from thiolactic acid, thioglycolic acid, cysteine, sodium sulfide, sodium sulfite, sodium thiosulfate, sodium dithionite, and/or the cosmetically acceptable salts thereof, and
- the coloring agent (F) includes at least one direct acid dye.

In this regard, a multicomponent packaging unit (kit) is preferred which comprises three separately packaged cosmetic agents (G), (K), and (F), wherein
- the straightening agent (G) includes at least one alkalizing agent selected from sodium hydroxide, potassium hydroxide, lithium hydroxide, magnesium hydroxide, calcium hydroxide, and/or guanidinium hydroxide,
- the conditioner (K) includes at least one reducing agent selected from thiolactic acid, thioglycolic acid, cysteine, sodium sulfide, sodium sulfite, sodium thiosulfate, sodium dithionite, and/or the cosmetically acceptable salts thereof, and
- the coloring agent (F) includes at least one direct acid dye.

In this regard, a multicomponent packaging unit (kit) is likewise preferred which comprises three separately packaged cosmetic agents (G), (K), and (F), wherein
- the straightening agent (G) includes at least one alkalizing agent selected from sodium hydroxide, potassium hydroxide, lithium hydroxide, magnesium hydroxide, calcium hydroxide, and/or guanidinium hydroxide,
- the coloring agent (F) includes at least one reducing agent selected from thiolactic acid, thioglycolic acid, cysteine, sodium sulfide, sodium sulfite, sodium thiosulfate, sodium dithionite, and/or the cosmetically acceptable salts thereof, and
- the coloring agent (F) includes at least one direct acid dye.

In this regard, a multicomponent packaging unit (kit) is likewise preferred which comprises three separately packaged cosmetic agents (G), (K), and (F), wherein
- the straightening agent (G) includes at least one alkalizing agent selected from sodium hydroxide, potassium hydroxide, lithium hydroxide, magnesium hydroxide, calcium hydroxide, and/or guanidinium hydroxide,
- the conditioner (K) and the coloring agent (F), independently of one another, each include at least one reducing agent selected from thiolactic acid, thioglycolic acid, cysteine, sodium sulfide, sodium sulfite, sodium thiosulfate, sodium dithionite, and/or the cosmetically acceptable salts thereof, and
- the coloring agent (F) includes at least one direct acid dye.

When the conditioner (K), which is used in the method according to the invention or provided in the multicomponent packaging unit (kit) according to the invention, is combined with one or more reducing agents, use thereof surprisingly results in minimized damage to the hair. The minimized damage to the hair is manifested in particular by a reduction in the cysteic acid content of the treated hair.

In this regard, use of the reducing agent(s) in certain quantity ranges has proven to be particularly advantageous in reducing damage to the hair.

In one particularly preferred embodiment, a method according to the invention is therefore characterized in that the conditioner (K) includes one or more reducing agents selected from thiolactic acid, thioglycolic acid, cysteine, and/or the physiologically acceptable salts thereof in an overall quantity of 0.1 to 10% by weight, preferably 0.5 to 8.5% by weight, more preferably 1.5 to 7.0% by weight, and particularly preferably 2.5 to 6.5% by weight, based on the total weight of the conditioner (K).

In addition, a particularly preferred multicomponent packaging unit (kit) is characterized in that the conditioner (K) includes one or more reducing agents selected from thiolactic acid, thioglycolic acid, cysteine, and/or the physiologically acceptable salts thereof in an overall quantity of 0.1 to 10% by weight, preferably 0.5 to 8.5% by weight, more preferably 1.5 to 7.0% by weight, and particularly preferably 2.5 to 6.5% by weight, based on the total weight of the conditioner (K).

In summary, a method of the first subject matter of the invention and a kit of the second subject matter of the invention are therefore very particularly preferably preferred, characterized in that the conditioner (K) includes one or more reducing agents selected from thiolactic acid, thioglycolic acid, cysteine, and/or the physiologically acceptable salts thereof in an overall quantity of 0.1 to 10% by weight, preferably 0.5 to 8.5% by weight, more preferably 1.5 to 7.0% by weight, and particularly preferably 2.5 to 6.5% by weight, based on the total weight of the conditioner (K).

Also, if the coloring agent (F), which is used in the method according to the invention or provided in the multicomponent packaging unit (kit) according to the invention, is combined with one or more reducing agents, use thereof surprisingly results in minimized damage to the hair. The minimized damage to the hair is similarly manifested by a reduction in the cysteic acid content of the treated hair. In this regard, use of the reducing agent(s) in certain quantity ranges has proven to be particularly advantageous in reducing damage to the hair.

In one particularly preferred embodiment, a method according to the invention is therefore characterized in that the coloring agent (F) includes one or more reducing agents selected from thiolactic acid, thioglycolic acid, cysteine, and/or the physiologically acceptable salts thereof in an overall quantity of 1.2 to 9% by weight, preferably 1.6 to 8.1% by weight, more preferably 2.1 to 6.6% by weight, and particularly preferably 2.6 to 6.2% by weight, based on the total weight of the coloring agent (F).

Furthermore, a particularly preferred multicomponent packaging unit (kit) is characterized in that the coloring agent (F) includes one or more reducing agents selected from thiolactic acid, thioglycolic acid, cysteine, and/or the physiologically acceptable salts thereof in an overall quantity of 1.2 to 9% by weight, preferably 1.6 to 8.1% by weight, more preferably 2.1 to 6.6% by weight, and particularly preferably 2.6 to 6.2% by weight, based on the total weight of the coloring agent (F).

In summary, a method of the first subject matter of the invention and a kit of the second subject matter of the invention are therefore very particularly preferably preferred, characterized in that the coloring agent (F) includes one or more reducing agents selected from thiolactic acid, thioglycolic acid, cysteine, and/or the physiologically acceptable salts thereof in an overall quantity of 1.2 to 9% by weight, preferably 1.6 to 8.1% by weight, more preferably 2.1 to 6.6% by weight, and particularly preferably 2.6 to 6.2% by weight, based on the total weight of the coloring agent (F).

Thiolactic acid is understood to mean D-thiolactic acid, L-thiolactic acid, and/or the mixture thereof. Cysteine is understood to mean D-cysteine, L-cysteine, and/or the mixture thereof.

Selected reducing agents have proven to be very particularly effective in avoiding or minimizing damage to the hair. In the measurement of straightened and dyed keratin fibers, particularly low cysteic acid values have been measured in particular when the reducing agent ammonium thiolactate is used. The level of cysteic acid in the keratin fiber is used as a measure for the extent of the damage: the lower the cysteic acid content, the better the condition of the hair.

Ammonium thiolactate is the ammonium salt of thiolactic acid (i.e., the ammonium salt of 2-sulfanylpropionic acid)

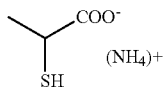

The definition of ammonium thiolactate includes the ammonium salts of D-thiolactic acid and also the salts of L-thiolactic acid, and the mixtures thereof.

In one particularly preferred embodiment, a method according to the invention is therefore characterized in that the conditioner (K) and/or the coloring agent (F) include(s) ammonium thiolactate as reducing agent in a quantity of 2.7 to 5.5% by weight, in each case based on the total weight of the conditioner (K) and the total weight of the coloring agent (F).

Furthermore, a particularly preferred multicomponent packaging unit (kit) is characterized in that the conditioner (K) and/or the coloring agent (F) include(s) ammonium thiolactate as reducing agent in a quantity of 2.7 to 5.5% by weight, in each case based on the total weight of the conditioner (K) and the total weight of the coloring agent (F).

In summary, a method of the first subject matter of the invention and a kit of the second subject matter of the invention are therefore very particularly preferred, characterized in that the conditioner (K) and/or the coloring agent (F) include(s) ammonium thiolactate as reducing agent in a quantity of 2.7 to 5.5% by weight, with the weight indication in each case based on the total weight of the agent in which the ammonium thiolactate is used.

If only the conditioner (K) includes ammonium thiolactate, the calculation of the quantity of ammonium thiolactate included in the conditioner (K) is carried out based on the total weight of the conditioner (K). If only the coloring agent (F) includes ammonium thiolactate, the calculation of the quantity of ammonium thiolactate included in the coloring agent (F) is carried out based on the total weight of the coloring agent (F). If both the conditioner (K) and the coloring agent (F) include ammonium thiolactate, the basis for calculation of the quantity of ammonium thiolactate included in the conditioner (K) is the total weight of the conditioner (K), and for the quantity of ammonium thiolactate included in the coloring agent (F), is the total weight of the coloring agent (F).

Accordingly, a method according to the invention for straightening and dyeing keratinous fibers is likewise preferred which comprises the following steps:
A) treating the fibers with a straightening agent (G),
B) treating the fibers with a conditioner (K),
C) treating the fibers with a coloring agent (F),
wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the conditioner (K) and/or the coloring agent (F) include(s) ammonium thiolactate as reducing agent in a quantity of 2.7 to 5.5% by weight, with the weight indication in each case based on the total weight of the agent in which the ammonium thiolactate is used, and
the coloring agent (F) includes at least one direct acid dye.

A method according to the invention for straightening and dyeing keratinous fibers is also particularly preferably preferred which comprises the following steps:
A) treating the fibers with a straightening agent (G),
B) treating the fibers with a conditioner (K),
C) treating the fibers with a coloring agent (F),
wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the conditioner (K) includes ammonium thiolactate as reducing agent in a quantity of 2.7 to 5.5% by weight, in each case based on the total weight of the conditioner (K),
the coloring agent (F) includes at least one direct acid dye.

A method according to the invention for straightening and dyeing keratinous fibers is also particularly preferably preferred which comprises the following steps:
A) treating the fibers with a straightening agent (G),
B) treating the fibers with a conditioner (K),
C) treating the fibers with a coloring agent (F),
wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the coloring agent (F) includes ammonium thiolactate as reducing agent in a quantity of 2.7 to 5.5% by weight, in each case based on the total weight of the coloring agent (F), and
the coloring agent (F) includes at least one direct acid dye.

A method according to the invention for straightening and dyeing keratinous fibers is also particularly preferably preferred which comprises the following steps:
A) treating the fibers with a straightening agent (G),
B) treating the fibers with a conditioner (K),
C) treating the fibers with a coloring agent (F),
wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the conditioner (K) and the coloring agent (F), independently of one another, include ammonium thiolactate as reducing agent in a quantity of 2.7 to 5.5% by weight, in each case based on the total weight of the conditioner (K) and the total weight of the coloring agent (F), and
the coloring agent (F) includes at least one direct acid dye.

In addition, a particularly preferred multicomponent packaging unit (kit) is characterized in that the conditioner (K) and/or the coloring agent (F) include(s) ammonium thiolactate as reducing agent in a quantity of 2.7 to 5.5% by weight, in each case based on the total weight of the conditioner (K) and the total weight of the coloring agent (F).

In addition, a multicomponent packaging unit (kit) according to the invention is particularly preferred which comprises three separately packaged cosmetic agents (G), (K), and (F), wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the conditioner (K) includes ammonium thiolactate as reducing agent in a quantity of 2.7 to 5.5% by weight, in each case based on the total weight of the conditioner (K), and
the coloring agent (F) includes at least one direct acid dye.

A multicomponent packaging unit (kit) according to the invention is also particularly preferred which comprises three separately packaged cosmetic agents (G), (K), and (F), wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the coloring agent (F) includes ammonium thiolactate as reducing agent in a quantity of 2.7 to 5.5% by weight, in each case based on the total weight of the coloring agent (F), and
the coloring agent (F) includes at least one direct acid dye.

A multicomponent packaging unit (kit) according to the invention is also particularly preferred which comprises three separately packaged cosmetic agents (G), (K), and (F), wherein
the straightening agent (G) includes at least one alkalizing agent selected from sodium hydroxide, potassium hydroxide, lithium hydroxide, magnesium hydroxide, calcium hydroxide, and/or guanidinium hydroxide,
the conditioner (K) and the coloring agent (F), independently of one another, include ammonium thiolactate as reducing agent in a quantity of 2.7 to 5.5% by weight, in each case based on the total weight of the conditioner (K) and the total weight of the coloring agent (F), and
the coloring agent (F) includes at least one direct acid dye.

In summary, a method of the first subject matter of the invention and a kit of the second subject matter of the invention are very particularly preferred, characterized in that the conditioner (K) and/or the coloring agent (F) include(s) ammonium thiolactate as reducing agent in a quantity of 2.7 to 5.5% by weight, with the weight indication in each case based on the total weight of the agent in which the ammonium thiolactate is used.

Furthermore, for the method according to the invention for straightening and dyeing the keratin fibers and for the corresponding multicomponent packaging unit, it is essential that the coloring agent (F) includes at least one direct acid dye.

Direct dyes may be subdivided into cationic dyes (basic dyes), nonionic dyes, and anionic dyes (also referred to as acid dyes), based on their charge.

Acid dyes are understood to mean direct dyes having at least one carboxylic acid group (—COOH) and/or one sulfonic acid group (—SO$_3$H). The protonated forms (—COOH, —SO$_3$H) of the carboxylic acid or sulfonic acid groups are present in equilibrium with their respective deprotonated forms (—COO$^-$, —SO$_3^-$), as a function of the pH. The proportion of the protonated forms increases with decreasing pH. When direct dyes in the form of their salts are used, the carboxylic acid groups or sulfonic acid groups are present in deprotonated form, and are neutralized with appropriate stoichiometric equivalents of cations (for example, Na cations or K cations) in order to maintain electroneutrality.

For example, one or more compounds from the following group may be selected as suitable acid dyes: Acid Yellow 1 (D&C Yellow 7, Citronin A, Ext. D&C Yellow No. 7, Japan Yellow 403, C.I. 10316, COLIPA n° B001), Acid Yellow 3 (COLIPA n°: C 54, D&C Yellow N° 10, Quinoline Yellow, E104, Food Yellow 13), Acid Yellow 9 (C.I. 13015), Acid Yellow 17 (C.I. 18965), Acid Yellow 23 (COLIPA n° C. 29, Covacap Jaune W 1100 (LCW), Sicovit Tartrazine 85 E 102 (BASF), tartrazine, Food Yellow 4, Japan Yellow 4, FD&C Yellow No. 5), Acid Yellow 36 (C.I. 13065), Acid Yellow 121 (C.I. 18690), Acid Orange 6 (C.I. 14270), Acid Orange 7 (2-naphthol orange, Orange II, C.I. 15510, D&C Orange 4, COLIPA n° C.015), Acid Orange 10 (C.I. 16230; Orange G sodium salt), Acid Orange 11 (C.I. 45370), Acid Orange 15 (C.I. 50120), Acid Orange 20 (C.I. 14600), Acid Orange 24 (Brown 1; C.I. 20170; KATSU201; nosodiumsalt; Brown No. 201; Resorcin Brown; Acid Orange 24; Japan Brown 201; D & C Brown No. 1), Acid Red 14 (C.I. 14720), Acid Red 18 (E124, Red 18; C.I. 16255), Acid Red 27 (E 123, C.I. 16185, C Red 46, Echtrot D, FD&C Red No. 2, Food Red 9, Naphthol Red S), Acid Red 33 (Red 33, Fuchsia Red, D&C Red 33, C.I. 17200), Acid Red 35 (C.I. 18065), Acid Red 51 (C.I. 45430, Pyrosin B, Tetraiodfluorescein, Eosin J, Iodeosin), Acid Red 52 (C.I. 45100, Food Red 106, Solar Rhodamine B, Acid Rhodamine B, Red n° 106 Pontacyl Brilliant Pink), Acid Red 73 (C.I. 27290), Acid Red 87 (Eosin, C.I. 45380), Acid Red 95 (C.I. 45425, Erythrosine, Simacid Erythrosine Y), Acid Red 184 (C.I. 15685), Acid Red 195, Acid Violet 43 (Jarocol Violet 43, Ext. D&C Violet n° 2, C.I. 60730, COLIPA n° C.063), Acid Violet 49 (C.I. 42640), Acid Violet 50 (C.I. 50325), Acid Blue 1 (Patent Blue, C.I. 42045), Acid Blue 3 (Patent Blue V, C.I. 42051), Acid Blue 7 (C.I. 42080), Acid Blue 104 (C.I. 42735), Acid Blue 9 (E 133, Patent Blue AE, Amido Blue AE, Erioglaucin A, C.I. 42090, C.I. Food Blue 2), Acid Blue 62 (C.I. 62045), Acid Blue 74 (E 132, C.I. 73015), Acid Blue 80 (C.I. 61585), Acid Green 3 (C.I. 42085, Foodgreenl), Acid Green 5 (C.I. 42095), Acid Green 9 (C.I 42100), Acid Green 22 (C.I. 42170), Acid Green 25 (C.I. 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, C.I. 20470, COLIPA n° B15), Acid Black 52 (C.I. 15711), Food Yellow 8 (C.I. 14270), Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

A very particularly preferred method of the first subject matter of the invention is characterized in that the coloring agent (F) includes at least one direct acid dye selected from Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2, and/or D&C Brown 1.

A very particularly preferred kit of the second subject matter of the invention is characterized in that the coloring agent (F) includes at least one direct acid dye selected from Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 7, D&C Orange 4, D&C Green 5, D&C Orange 10, D&C Orange 11, D&C Red 21, D&C Red 27, D&C Red 33, D&C Violet 2, and/or D&C Brown 1.

In summary, a method of the first subject matter of the invention and a kit of the second subject matter of the invention are very particularly preferred, characterized in that the coloring agent (F) includes at least one direct acid dye selected from Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2, and/or D&C Brown 1.

The acid dye(s) may preferably be included in the coloring agent in an overall quantity of 0.01 to 5.5% by weight, preferably 0.08 to 4.7% by weight, more preferably 0.2 to 3.4% by weight, and particularly preferably 0.4 to 1.8% by weight. The basis for calculation of the overall quantity of the acid dyes is the total weight of the coloring agent (F).

Therefore, a method of the first subject matter of the invention and a kit of the second subject matter of the invention are also particularly preferred, characterized in that the coloring agent (F) includes the direct acid dye(s) in an overall quantity of 0.01 to 5.5% by weight, preferably 0.08 to 4.7% by weight, more preferably 0.2 to 3.4% by weight, and particularly preferably 0.4 to 1.8% by weight, based on the total weight of the coloring agent (F).

The straightening agent (G) according to the invention includes one or more hydroxides from the above-described group. These are strong bases. Accordingly, the straightening agent (G) also has an alkaline pH. Particularly good straightening is achieved when the straightening agent (G) has a pH of 8.5 to 13.4, preferably 9.5 to 13.3, more preferably 10.5 to 13.2, and particularly preferably 11.5 to 13.0.

The pH may be measured using a glass electrode, which typically is designed in the form of a combination electrode. The pH values in the present invention are pH values that have been measured at a temperature of 22° C.

A preferred method of the first subject matter of the invention is characterized in that the straightening agent (G) has a pH of 8.5 to 13.4, preferably 9.5 to 13.3, more preferably 10.5 to 13.2, and particularly preferably 11.5 to 13.0.

A preferred kit of the second subject matter of the invention is characterized in that the straightening agent (G) has a pH of 8.5 to 13.4, preferably 9.5 to 13.3, more preferably 10.5 to 13.2, and particularly preferably 11.5 to 13.0.

In summary, a method of the first subject matter of the invention and a kit of the second subject matter of the invention are very particularly preferred, characterized in that the straightening agent (G) has a pH of 8.5 to 13.4, preferably 9.5 to 13.3, more preferably 10.5 to 13.2, and particularly preferably 11.5 to 13.0.

The conditioner (K) is also advantageously set to a certain pH. It has been found that use of conditioners (K) with a pH between 2.0 and 7.5 has the most advantages with regard to the reduction of damage to the hair. The conditioner is preferably set to a pH of 3.0 to 6.5; a particularly low level of damage is obtained at pH values in the range of 3.5 to 5.5.

A preferred method of the first subject matter of the invention is characterized in that the conditioner (K) has a pH of 2.0 to 7.5, preferably 2.5 to 7.0, more preferably 3.0 to 6.5, and particularly preferably 3.5 to 5.5.

Similarly, a preferred kit of the second subject matter of the invention is characterized in that the conditioner (K) has a pH of 2.0 to 7.5, preferably 2.5 to 7.0, more preferably 3.0 to 6.5, and particularly preferably 3.5 to 5.5.

In summary, a method of the first subject matter of the invention and a kit of the second subject matter of the invention are very particularly preferred, characterized in that the conditioner (K) has a pH of 2.0 to 7.5, preferably 2.5 to 7.0, more preferably 3.0 to 6.5, and particularly preferably 3.5 to 5.5.

The pH of the coloring agent (F) is preferably in the acidic range. The acidic pH range has a favorable effect not only with regard to the color intensity of the coloration obtainable with the acid dyes, but also in particular with regard to the reduction of damage to the hair. The pH of the coloring agent (F) preferably has a value of 1.5 to 6.0, preferably 1.6 to 5.2, more preferably 1.7 to 4.0, and particularly preferably 1.8 to 2.5.

A preferred method of the first subject matter of the invention is characterized in that the coloring agent (F) has a pH of 1.5 to 6.0, preferably 1.6 to 5.2, more preferably 1.7 to 4.0, and particularly preferably 1.8 to 2.5.

Similarly, a preferred kit of the second subject matter of the invention is characterized in that the coloring agent (F) has a pH of 1.5 to 6.0, preferably 1.6 to 5.2, more preferably 1.7 to 4.0, and particularly preferably 1.8 to 2.5.

In summary, a method of the first subject matter of the invention and a kit of the second subject matter of the invention are very particularly preferred, characterized in that the coloring agent (F) has a pH of 1.5 to 6.0, preferably 1.6 to 5.2, more preferably 1.7 to 4.0, and particularly preferably 1.8 to 2.5.

A method according to the invention for straightening and dyeing keratinous fibers is explicitly very particularly preferred which comprises the following steps:
A) treating the fibers with a straightening agent (G),
B) treating the fibers with a conditioner (K),
C) treating the fibers with a coloring agent (F),
wherein
- the straightening agent (G) includes at least one alkalizing agent selected from sodium hydroxide, potassium hydroxide, lithium hydroxide, magnesium hydroxide, calcium hydroxide, and/or guanidinium hydroxide and has a pH of 11.5 to 13.0,
- the conditioner (K) and/or the coloring agent (F) include(s) ammonium thiolactate as reducing agent in a quantity of 2.7 to 5.5% by weight, in each case based on the total weight of the conditioner (K) and the total weight of the coloring agent (F),
- the conditioner (K) has a pH of 3.5 to 5.5,
- the coloring agent (F) includes at least one direct acid dye includes and has a pH of 1.8 to 2.5.

The straightening agent (G) is a hydroxide-based product, and the straightening agent (G) itself is free of reducing agents.

Therefore, a method according to the invention and a kit according to the invention are preferred which in each case are characterized in that the straightening agent (G) is free of reducing agents selected from thiolactic acid, thioglycolic acid, cysteine, sodium sulfide, sodium sulfite, sodium thio sulfate, sodium dithionite, and the cosmetically acceptable salts thereof.

Within the meaning of the present invention, the definition "free of reducing agents" is understood to mean that the overall quantity of the reducing agents from the above-mentioned group is less than 0.25% by weight, preferably less than 0.1% by weight, and particularly preferably less than 0.05% by weight, based on the total weight of the straightening agent (G).

Furthermore, it is also preferred when the straightening agent is also free of further reducing agents such as ascorbic acid. It is therefore preferred when the straightening agent (G) includes less than 0.25% by weight, preferably less than 0.1% by weight, and particularly preferably less than 0.05% by weight, of ascorbic acid, based on the total weight of the straightening agent (G).

A preferred method according to the invention and a preferred kit according to the invention are therefore further characterized in that the straightening agent (G) is free of reducing agents selected from thiolactic acid, thioglycolic acid, cysteine, sodium sulfide, sodium sulfite, sodium thiosulfate, sodium dithionite, and the salts thereof.

In other words, a preferred method according to the invention and a preferred kit according to the invention are therefore further characterized in that the overall quantity of the reducing agents selected from thiolactic acid, thioglycolic acid, cysteine, sodium sulfide, sodium sulfite, sodium thiosulfate, sodium dithionite, and the salts thereof in the straightening agent (G) is less than 0.25% by weight, preferably less than 0.1% by weight, and particularly preferably less than 0.05% by weight, based on the total weight of the straightening agent (G).

The straightening agent (G), the conditioner (K), and/or the coloring agent (F) may also include further active substances, auxiliary substances, and additives in order to improve the coloring power and to set further desired properties in the agent.

The agents (G), (K), and/or (F) are preferably provided as a liquid preparation, and optionally a further surface-active substance is additionally added to the agents; depending on the field of application, such surface-active substances are referred to as surfactants or as emulsifiers. They are preferably selected from anionic, zwitterionic, amphoteric, and nonionic surfactants and emulsifiers.

Agents which are suitable according to the invention are characterized in that the agent additionally includes at least one anionic surfactant. Preferred anionic surfactants are fatty acids, alkyl sulfates, alkyl ether sulfates, and ether carboxylic acids that include 10 to 20 C atoms in the alkyl group and up to 16 glycol ether groups in the molecule. The anionic surfactants are used in proportions of 0.1 to 45% by weight, preferably 1 to 30% by weight, and very particularly preferably 1 to 15% by weight, based on the overall quantity of the ready-to-apply agent.

Agents which are suitable according to the invention are characterized in that the agent additionally includes at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines. One preferred zwitterionic surfactant is known by the INCI name Cocamidopropyl Betaine.

Agents which are suitable according to the invention are characterized in that the agent additionally includes at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids. Particularly preferred amphoteric surfactants are N-cocoalkylamino propionate, cocoacylaminoethylamino propionate, and $C_{12}$-$C_{18}$ acyl sarcosine.

In addition, it has proven to be advantageous when the agents include further, noniogenic surface-active substances. Preferred nonionic surfactants are alkyl polyglycosides and alkylene oxide addition products with fatty alcohols and fatty acids in each case having 2 to 30 mol ethylene oxide per mol fatty alcohol or fatty acid. Preparations having excellent properties are likewise obtained when they include fatty acid esters of ethoxylated glycerin as nonionic surfactants.

The nonionic, zwitterionic, or amphoteric surfactants are used in proportions of 0.1 to 45% by weight, preferably 1 to 30% by weight, and very particularly preferably 1 to 15% by weight, based on the total quantity of the agents (G), (K), and (F).

It has likewise proven to be advantageous when the agents include at least one thickener. In principle, there are no limitations with regard to these thickeners. Organic as well as strictly inorganic thickeners may be used.

Suitable thickeners are anionic synthetic polymers; cationic synthetic polymers; naturally occurring thickeners, such as nonionic guar gums, scleroglucan gums, or xanthan gums, gum arabic, gum ghatti, karaya gum, gum tragacanth, carrageenan gum, agar-agar, locust bean gum, pectins, alginates, starch fractions, and derivatives such as amylose, amylopectin, and dextrins, and cellulose derivatives such as methylcellulose, carboxyalkyl celluloses, and hydroxyalkyl celluloses; nonionic synthetic polymers such as polyvinyl alcohol or polyvinylpyrrolidinone; and inorganic thickeners, in particular phyllosilicates such as bentonite, in particular smectites such as montmorillonite or hectorite.

The agents (G), (K), and/or (F) may also include anionic polymeric thickeners. Suitable compounds are selected, for example, from the crosslinked or noncrosslinked copolymers formed from at least two different monomers selected from acrylic acid, methacrylic acid, the $C_1$-$C_6$ alkyl esters of acrylic acid, and/or the $C_1$-$C_6$ alkyl esters of methacrylic acid. Particularly preferred anionic copolymers are copolymers of acrylic acid, methacrylic acid, or the $C_1$-$C_6$ alkyl esters thereof, which are marketed under the INCI designation Acrylates Copolymer. In particular, the combination of methacrylic acid and ethyl acrylate and optionally, cross-linking multifunctional monomers, is preferred. Aculyn® 33 or 33A, offered by Rohm & Haas, is one example of a preferred commercial product.

It is also advantageous when the conditioner (K) includes at least one cationic polymer and/or cationic surfactant.

Therefore, a method of the first subject matter of the invention or a kit of the second subject matter of the invention is also very particularly preferred, characterized in that the conditioner (K) includes at least one cationic polymer and/or cationic surfactant.

With regard to minimizing the damage to hair, it has found be advantageous in particular when the conditioner (K) includes one or more polymers selected from Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquarternium-64, Polyquaternium-67, Polyquaternium-68, Polyquaternium-69, and/or Polyquaternium-86.

Therefore, a method of the first subject matter of the invention or a kit of the second subject matter of the invention is also very particularly preferred, characterized in that the conditioner (K) includes one or more polymers selected from Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquarternium-64, Polyquaternium-67, Polyquaternium-68, Polyquaternium-69, and/or Polyquaternium-86.

Therefore, a method of the first subject matter of the invention and a kit of the second subject matter of the invention are also very particularly preferred, characterized in that the conditioner (K) includes one or more polymers selected from Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquarternium-64, Polyquaternium-67, Polyquaternium-68, Polyquaternium-69, and/or Polyquaternium-86.

Methods and kits preferred according to the invention are characterized in that the agents (G), (K), and/or (F) additionally include one or more cationic surfactants. According to the invention, all cationic surfactants which are customary and known to those skilled in the art may be used as cationic surfactants. These include:

quaternary imidazoline compounds. Formula Quimi-I below shows the structure of these compounds.

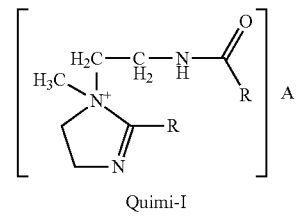

Quimi-I

The R moieties each independently stand for a saturated or unsaturated, linear or branched hydrocarbon moiety having a chain length of 8 to 30 carbon atoms. The preferred compounds of formula I each include the same hydrocarbon moiety for R. The chain length of the R moieties is preferably 12 to 21 carbon atoms. Particularly preferred examples according to the invention are available under the INCI designations Quaternium-27, Quaternium-72, Quaternium-83, and Quaternium-91.

cationic surfactants according to formula (Tkat-2), $$RCO-X-N^+R^1R^2R^3A^- \quad \text{(Tkat-2)}$$

In the formula, R stands for a substituted or unsubstituted, branched or straight-chain alkyl or alkenyl moiety having 11 to 35 carbon atoms in the chain, X stands for —O— or —NR$^5$—, R$^1$ stands for an alkylene group having 2 to 6 C atoms, which may be unsubstituted or substituted, wherein in the event of substitution, substitution with an —OH or —NH group is preferred, R$^2$, R$^3$ each independently stand for an alkyl or hydroxyalkyl group having 1 to up to 6 C atoms in the chain, wherein the chain may be linear or branched, R5 stands for hydrogen or a C1 to C6 straight-chain or branched, alkyl or alkenyl moiety, which may also be substituted by a hydroxy group. Within this structure class, the compounds of one of the following structures are preferably used:

$$CH_3(CH_2)_{20}CONH(CH_2)_3-N^+(CH_3)_2-CH_2CH_3A^- \quad \text{(Tkat-3)}$$

$$CH_3(CH_2)_{20}CONH(CH_2)_3-N^+(CH_3)_2-CH_2 \\ (CHOH)CH_2OH\ A^- \quad \text{(Tkat-4)}$$

$$CH_3(CH_2)_{20}COOCH_2CHOHCH_2-N^+(CH_3)_3A^- \quad \text{(Tkat-5)}$$

$$CH_3(CH_2)_{20}CONH(CH_2)_3-N^+(CH_3)_2- \\ CH_2CH_2OHA^- \quad \text{(Tkat-6)}$$

Examples of such commercial products are Schercoquat BAS, Lexquat AMG-BEO, Akypoquat 131, or Incroquat Behenyl HE.

Esterquats according to formula (Tkat1-2) are used.

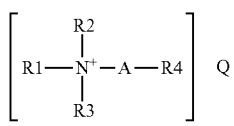 (Tkat 1-2)

In the formula, the moieties R1, R2, and R3 are in each case independent of one another, and may be the same or different. The moieties R1, R2, and R3 mean the following:
- a branched or unbranched alkyl moiety which includes 1 to 4 carbon atoms, and which may include at least one hydroxyl group, or
- a saturated or unsaturated, branched or unbranched or a cyclic, saturated or unsaturated alkyl moiety which includes 6 to 30 carbon atoms, and which may include at least one hydroxyl group, or
- an aryl or alkaryl moiety, for example phenyl or benzyl, the moiety (-A-R4), with the condition that at most two of the moieties R1, R2, or R3 may stand for this moiety:

The moiety -(A-R4) is included at least 1 to 3 times.
In this term, A stands for:
1) $-(CH2)_n-$, where n=1 to 20, preferably n=1 to 10, and particularly preferably n=1 to 5, or
2) $-(CH2-CHR5-O)_n-$, where n=1 to 200, preferably 1 to 100, particularly preferably 1 to 50, and very particularly preferably 1 to 20, where R5 means hydrogen, methyl, or ethyl, and R4 stands for:
1) R6-O-CO-, where R6 is a saturated or unsaturated, branched or unbranched, or a cyclic saturated or unsaturated, alkyl moiety which includes 6 to 30 carbon atoms, and which may include at least one hydroxy group, and which may optionally also be oxyethylated with 1 to 100 ethylene oxide units and/or 1 to 100 propylene oxide units, or
2) R7-CO-, where R7 is a saturated or unsaturated, branched or unbranched, or a cyclic saturated or unsaturated, alkyl moiety which includes 6 to 30 carbon atoms, and which may include at least one hydroxy group, and which may optionally also be oxyethylated with 1 to 100 ethylene oxide units and/or 1 to 100 propylene oxide units, and Q stands for a physiologically acceptable organic or inorganic anion.

Such products are marketed under the trademarks Rewoquat®, Stepantex®, Dehyquart®, and Armocare®, for example. The products Armocare® VGH-70, an N,N-bis(2-palmitoyloxyethyl)dimethylammonium chloride, and Dehyquart® F-75, Dehyquart® C-4046, Dehyquart® L80, Dehyquart® F-30, Dehyquart® AU-35, Rewoquat®WE18, Rewoquat® WE38 DPG, and Stepantex® VS 90 are examples of such esterquats. Further compounds of formula (Tkat1-2) particularly preferred according to the invention include those of formula (Tkat1-2.1), the cationic betaine esters.

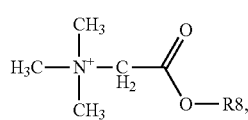 (Tkat1-2.1)

in which R8 has the same meaning as R7.

monoalkyltrimethylammonium salts having an alkyl moiety chain length of 16 to 24 carbon atoms, corresponding to formula (Tkat1-1),

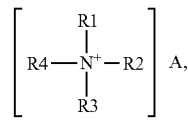 (Tkat 1-2)

in which R1, R2, and R3 each stand for a methyl group, and R4 stands for a saturated, branched or unbranched alkyl moiety having a chain length of 16 to 24 carbon atoms. Examples of compounds of formula (Tkat1-1) are cetyltrimethylammonium chloride, cetyltrimethylammonium bromide, cetyltrimethylammonium methosulfate, stearyltrimethylammonium chloride, behenyltrimethylammonium chloride, behenyltrimethylammonium bromide, and behenyltrimethylammonium methosulfate.

amines and/or cationized amines, in particular an amidoamine and/or a cationized amidoamine having the following structural formulas:

$$R^1-NH-(CH_2)_n-NR^2R^3 \quad \text{(Tkat7) and/or}$$

$$R^1-NH-(CH_2)_n-NR^2R^3R^4 \quad \text{(Tkat8),}$$

where R1 is an acyl or alkyl moiety which includes 6 to 30 C atoms, and which may be branched or unbranched, saturated or unsaturated, and wherein the acyl moiety and/or the alkyl moiety may include at least one OH group, and R2, R3, and R4 are each independently hydrogen or an alkyl moiety which includes 1 to 4 C atoms, and which may be the same or different, saturated or unsaturated, and
$X^-$ means an anion and
n means an integer between 1 and 10.

A composition is preferred in which the amine and/or the quaternized amine according to general formulas (Tkat7) and/or (Tkat8) is an amidoamine and/or a quaternized amidoamine in which R1 means a branched or unbranched, saturated or unsaturated acyl moiety which includes 6 to 30 C atoms, and which may include at least one OH group. A fatty acid moiety including oils and waxes, in particular naturally oils and waxes, is preferred. Suitable examples are lanolin, beeswax, or candelilla wax. Also preferred are those amidoamines and/or quaternized amidoamines in which R2, R3, and/or R4 in formulas (Tkat7) and/or (Tkat8) mean(s) a moiety according to general formula $CH_2CH_2OR5$, where R5 may mean alkyl moieties having 1 to 4 carbon atoms, hydroxyethyl, or hydrogen. In general formulas (Tkat7) and/or (Tkat8), n is preferably an integer between 2 and 5. Also preferred are amidoamines and/or quaternized amidoamines of general formulas (Tkat7) and/or (Tkat8), in which the anion $X^-$ is a halide ion or a compound of general formula $RSO_3^-$, where R means saturated or unsaturated alkyl moieties having 1 to 4 carbon atoms. The alkyl moiety having 1 to 4 carbon atoms in R2, R3, and R4 and/or the alkyl moiety having 1 to 4 carbon atoms in $RSO_3^-$ in general formula (Tkat7) and/or (Tkat8) may include at least one hydroxyl group. The alkylamidoamines may be present as such, and may also be converted to a quaternary compound in the composition by protonation in an appropriately acidic solution. The cationic alkylamidoamines are preferred according to the invention.

The following are examples of amidoamines to be used according to the invention, which may optionally be quaternized: Witcamine® 100 (Witco, INCI designation: Cocamidopropyl Dimethylamine), Incromine® BB (Croda, INCI designation: Behenamidopropyl Dimethylamine), Mackine® 401 (McIntyre, INCI designation: Isostearylamidopropyl Dimethylamine) and other Mackine types, Adogen® S18V (Witco, INCI designation: Stearylamidopropyl Dimethylamine), and the following are examples of permanent cationic aminoamines: Rewoquat® RTM 50 (Witco Surfactants GmbH, INCI designation: Ricinoleamidopropyltrimonium Methosulfate), Empigen® CSC (Albright & Wilson, INCI designation: Cocamidopropyltrimonium Chloride), Swanol® Lanoquat DES-50 (Nikko, INCI designation: Quaternium-33), Rewoquat® UTM 50 (Witco Surfactants GmbH, Undecyleneamidopropyltrimonium Methosulfate).

The anion of all the cationic compounds described above is selected from the physiologically acceptable anions. Examples of such include the halide ions fluoride, chloride, and bromide, sulfates of general formula $RSO_3^-$, where R means saturated or unsaturated alkyl moieties having 1 to 4 carbon atoms, or anionic moieties of organic acids such as maleate, fumarate, oxalate, tartrate, citrate, lactate, or acetate.

Cationic imidazolines, esterquats, cationic surfactants according to formula (Tkat-2), and amines and/or cationized amines, in particular amidoamines and/or cationized amidoamines, are preferably used.

The cationic surfactants mentioned above may be used individually or in any given combinations with one another, included in quantities between 0.01 to 20% by weight, preferably in quantities of 0.01 to 10% by weight, and very particularly preferably in quantities of 0.1 to 7.5% by weight. The best results are obtained with quantities of 0.1 to 5% by weight, in each case based on the overall composition of the particular agent.

The surfactants (T) are used in an overall surfactant quantity of 0.05-45% by weight, preferably 0.1-30% by weight, and very particularly preferably 0.5-25% by weight, based on the overall agent used according to the invention.

The cationic surfactants are used in quantities of 0.1 to 45% by weight, preferably 1 to 30% by weight, and very particularly preferably 1 to 15% by weight, in each case based on the overall quantity of the respective agent (G), (K), and/or (F).

In addition, the agents according to the invention may include further active substances, auxiliary substances, and additives, for example fatty alcohols, nonionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or nonvolatile, straight-chain, branched, or cyclic, crosslinked or noncrosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy, and/or hydroxyl groups (dimethicone copolyols), linear polysiloxane (A)-polyoxyalkylene (B) block copolymers, grafted silicone polymers; cationic polymers such as quaternized cellulose ethers, polysiloxanes having quaternary groups, dimethyldiallyl ammonium chloride polymers, acrylamide dimethyldiallyl ammonium chloride copolymers, dimethylaminoethyl methacrylate-vinylpyrrolidinone copolymers quaternized with diethyl sulfate, vinylpyrrolidinone-imidazolinium methochloride copolymers, and quaternized polyvinyl alcohol; zwitterionic and amphoteric polymers; anionic polymers, for example polyacrylic acids or crosslinked polyacrylic acids; structurizers such as glucose, maleic acid, and lactic acid, hair conditioning compounds such as phospholipids, for example lecithin and cephalins; fragrance oils, dimethyl isosorbide, and cyclodextrins; fiber structure-improving active substances, in particular mono-, di-, and oligosaccharides such as glucose, galactose, fructose, fruit sugar, and lactose; dyes for coloring the agent; anti-dandruff active substances such as piroctone olamine, zinc omadine, and climbazole; amino acids and oligopeptides; animal- and/or plant-based protein hydrolysates, and in the form of their fatty acid condensation products or optionally anionically or cationically modified derivatives; plant oils; light protection agents and UV blockers; active substances such as panthenol, pantothenic acid, pantolactone, allantoin, pyrrolidinone carboxylic acids and the salts thereof, and bisabolol; polyphenols, in particular hydroxycinnamic acids, 6,7-dihydroxycoumarin, hydroxybenzoic acids, catechins, tannins, leucoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling agents and penetration agents such as glycerin, propylene glycol monoethyl ether, carbonates, hydrogen carbonates, guanidines, ureas, and primary, secondary, and tertiary phosphates; opacifiers such as latex, styrene/PVP and styrene/acrylamide copolymers; pearlescence agents such as ethylene glycol mono- and distearate and PEG-3-distearate; pigments, and propellants such as propane-butane mixtures, $N_2O$, dimethyl ether, $CO_2$, and air.

Those skilled in the art will select these further substances according to the desired properties of the agents. With regard to further optional components and the quantities of these components used, explicit reference is made to relevant handbooks known to those skilled in the art. The additional active substances and auxiliary substances are preferably used in the agents according to the invention in each case in quantities of 0.0001 to 25% by weight, in particular 0.0005 to 15% by weight, in each case based on the total weight of the application mixture.

The above-described methods and kits according to the invention do not involve methods that include an oxidation step. Therefore, the method is explicitly differentiated from customary permanent wave methods and oxidative dyeing processes; i.e., no hydrogen peroxide is used.

To avoid further damage to the hair, the agents (G), (K), and (F) according to the invention are therefore also free of oxidizing agents, in particular free of hydrogen peroxide.

A preferred method according to the invention and a preferred kit according to the invention are therefore further characterized in that
- the overall quantity of hydrogen peroxide in the straightening agent (G) is less than 0.1% by weight, based on the total weight of the straightening agent (G),
- the overall quantity of hydrogen peroxide in the conditioner (K) is less than 0.1% by weight, based on the total weight of the conditioner (K), and
- the overall quantity of hydrogen peroxide in the coloring agent (F) is less than 0.1% by weight, based on the total weight of the coloring agent (F).

It has been shown that the multicomponent packaging units of the second subject matter of the invention are very well suited for low-damage straightening and dyeing of keratin fibers.

A further subject matter of the present invention is therefore the use of a multicomponent packaging unit (kit) of the second subject matter of the invention for reducing the damage during straightening and dyeing of keratinous fibers.

The statements concerning the method and the kit according to the invention apply mutatis mutandis with regard to further preferred embodiments of the method according to the invention.

Examples

The following formulations were produced. All information is in percent by weight unless indicated otherwise.

1. Straightening agent (G)

| Straightening agent (G) | % by weight |
|---|---|
| Paraffinum Liquidum | 10.0 |
| Cetearyl alcohol ($C_{16}/C_{18}$ fatty alcohols) | 9.0 |
| Sodium cetearyl sulfate | 1.0 |
| Propylene glycol | 6.0 |
| Weichceresin FL 400 (petrolatum) | 15.0 |
| Sodium hydroxide | 2.4 |
| Plantacare 2000 UP (decyl glucoside, 51-55% solution in water) | 0.8 |
| Laureth-4 | 1.0 |
| Polyquaternium-22 (39-43% solution in water) | 0.10 |
| Plantasil Relaxcare[1] | 1.00 |
| Hydrolyzed keratin | 0.30 |
| Beeswax | 0.50 |
| *Aloe vera* extract | 0.60 |
| Fragrance | q.s. |
| Water (distilled) | ad 100 |

[1]Plantasil Relaxcare, BASF, INCI: Potassium Silicates, Caprylyl/Capryl Glucoside, Glycerin

2. Conditioner (K)

| Conditioner (K) | K(V) % by weight (comparison) | K(E) % by weight according to the invention |
|---|---|---|
| Isopropyl myristate | 0.8 | 0.8 |
| Cetearyl alcohol ($C_{16}/C_{18}$ fatty alcohols) | 3.0 | 3.0 |
| Dehyquart F75[2] | 1.0 | 1.0 |
| Varisoft W 757 PG[3] | 4.0 | 4.0 |
| Citric acid, monohydrate | 0.5 | 0.5 |
| Stearamidopropyl dimethylamine | 0.4 | 0.4 |
| Methylparaben | 0.3 | 0.3 |
| Cos media CTH[4] | 0.5 | 0.5 |
| Hydrolyzed keratin | 0.1 | 0.1 |
| Croquat WKP PE LQ[5] | 0.1 | 0.1 |
| D-Panthenol (75% solution in water) | 0.2 | 0.2 |
| Ammonium thiolactate (70% solution in water) | — | 5.0 |
| Phenoxyethanol | 0.4 | 0.4 |
| Fragrance | q.s. | q.s. |
| Water | ad 100 | ad 100 |

[2]Dehyquart F75, BASF, INCI: Distearoylethyl Hydroxyethylmonium Methosulfate, Cetearyl Alcohol
[3]Varisoft W 757 PG, Evonic, INCI: Quaternium-27, Propylene Glycol
[4]Cosmedia CTH, BASF, INCI: Polyquaternium-37, Propylene Glycol Dicaprylate/Dicaprate, PPG-1 Trideceth-6
[5]Croquat WKP PE LQ, Croda, INCI: Cocodimonium Hydroxypropyl Hydrolyzed Keratin (30.0-38.0% solids)

3. Coloring agent (F)

| Coloring agent (F) | F(V) % by weight (comparison) | F(E) % by weight according to the invention |
|---|---|---|
| Ceteareth-12 | 2.6 | 2.6 |
| Phenoxyethanol | 0.81 | 0.81 |
| Etidronic acid (60% solution in water) | 2.1 | 2.1 |
| Xanthan | 1.35 | 1.35 |
| Sepigel 305[6] | 0.45 | 0.45 |
| Propylene carbonate | 5.0 | 5.0 |
| Acid Black No. 1 (C.l. 20470) | 0.2 | 0.2 |
| Acid Violet 43 (C.I. 60730, Ext. D&C Violet No. 2) | 0.07 | 0.07 |
| Acid Orange 7 (D&C Orange No. 4, C.I. 15510) | 0.4 | 0.4 |
| Ammonium thiolactate (70% solution in water) | — | 5.0 |
| Fragrance | q.s. | q.s. |
| Water | ad 100 | ad 100 |

[6]Sepigel 305, SEPPIC, INCI: Polyacrylamide, C13-14 Isoparaffin, Laureth-7 (45-49% solids)

4. Application

The straightening agent (G) was applied to hair strands (Kerling 6-0), left there for 20 minutes, and subsequently rinsed out with water. A conditioner (K(V) or K(E)) was then applied in each case to the strands, left there for 10 minutes, and subsequently rinsed out with water. The strands were then treated in each case with a coloring agent (F(V) or F(E)) for 40 minutes. After the treatment, the coloring agent was rinsed out.

5. Measurement of Damage to the Treated Hair Strands

For measuring the damage to the hair caused by the combined straightening and dyeing, the cysteic acid value of each treated hair strand was determined by quantitative NIR spectroscopy.

The spectra were recorded using an MPA™ FT-NIR spectrometer from Bruker Optik GmbH. The infrared range includes the wavelength range from 12,500 $cm^{-1}$ to 4000 $cm^{-1}$, and is characteristic for harmonic and combination vibrations of CH, OH, and NH groups, for example.

The samples were measured with an integration module at six different sample positions in diffuse reflection. The wavelength range of 7300 $cm^{-1}$ to 4020 $cm^{-1}$ was selected for the analysis of the measured NIR spectra.

The NIR spectra of cystine show characteristic absorption bands in the wavelength range of 6200 $cm^{-1}$ to 5500 $cm^{-1}$. A change in the hair due to severe damage (i.e., an increase in the cysteic acid content in the hair) results in bands at 5020 $cm^{-1}$ to 4020 $cm^{-1}$ in the NIR spectra which are characteristic for cysteic acid. The quantitative evaluation of the MR spectra was carried out by computer.

For each straightening-dyeing method, in each case three hair strands were treated and measured, and in each case the average was formed from these three measurements.

NIR analytical value [mol cysteic acid/100 mol amino acid]

| No. | Application | | Mol cysteic acid/ 100 mol amino acid | Average |
|---|---|---|---|---|
| 1 | (G) + K(V) + F(V) | Comparison: conditioner and coloring agent without ammonium thiolactate | 1.2<br>1.3<br>1.4 | 1.3 |
| 2 | (G) + K(E) + F(V) | According to the invention: conditioner with ammonium thiolactate | 1.2<br>1.1<br>1.0 | 1.1 |

-continued

NIR analytical value [mol cysteic acid/100 mol amino acid]

| No. | Application | | Mol cysteic acid/ 100 mol amino acid | Average |
|---|---|---|---|---|
| 3 | (G) + K(V) + F(E) | According to the invention: coloring agent with ammonium thiolactate | 1.1 1.1 1.1 | 1.1 |
| 4 | (G) + K(E) + F(E) | According to the invention: conditioner and coloring agent with ammonium thiolactate | 0.9 0.9 0.9 | 0.9 |

The hair strands treated using the method according to the invention, i.e., using the kit according to the invention (test Nos. 2, 3, and 4), showed reduced cysteic acid content, and thus reduced damage to the hair, compared to the comparison test (No. 1).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for straightening and dyeing keratinous fibers, including the following steps:
A1) treating the fibers with a straightening agent (G) having a pH of 8.5 to 13.4,
A2) allowing the straightening agent (G) to act for a period of 30 seconds to 45 minutes,
A3) rinsing out the straightening agent (G),
B1) treating the fibers with a conditioner (K) having a pH of 2.0 to 7.5,
B2) allowing the conditioner (K) to act for a period of 30 seconds to 45 minutes,
B3) rinsing out the conditioner (K),
C1) treating the fibers with a coloring agent (F),
C2) allowing the coloring agent to act for a period of 30 seconds to 45 minutes,
C3) rinsing out the coloring agent (F),
wherein the steps are performed in the stated order: A1), A2), A3), B1), B2), B3), C1), C2), and C3)
there is a time interval of 10 seconds to 48 hours between steps A3) and B1) and
there is a time interval of 10 seconds to 48 hours between steps B3) and C1), and
wherein
the straightening agent (G) includes at least one alkalizing agent selected from the group consisting of sodium hydroxide, potassium hydroxide, lithium hydroxide, magnesium hydroxide, calcium hydroxide, and guanidinium hydroxide,
the conditioner (K) and the coloring agent (F) each include ammonium thiolactate as a reducing agent in a quantity of 2.7 to 5.5% by weight, with the weight indication in each case based on the total weight of the conditioner and of the coloring agent in which the ammonium thiolactate is used,
the coloring agent (F) includes at least one direct acid dye in an amount of from 0.01 to 5.5% by weight based on the total weight of the coloring agent (F) and has a pH of 1.5 to 6.0,
wherein the agents (G), (F), and/or conditioner (K) further include a cationic surfactant comprising one or more quaternary imidazoline compounds, and
wherein the method does not include an oxidation step.

2. The method according to claim 1, wherein the conditioner (K) further includes one or more reducing agents selected from the group consisting of thiolactic acid, thioglycolic acid, cysteine and the physiologically acceptable salts thereof.

3. The method according to claim 1, wherein the coloring agent (F) further includes one or more reducing agents selected from the group consisting of thiolactic acid, thioglycolic acid, cysteine, and the physiologically acceptable salts thereof.

4. The method according to claim 1, wherein the at least one direct acid dye is selected from the group consisting of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2, and D&C Brown 1.

5. The method according to claim 1, wherein the straightening agent (G) is free of reducing agents selected from the group consisting of thiolactic acid, thioglycolic acid, cysteine, sodium sulfide, sodium sulfite, sodium thiosulfate, sodium dithionite, and the salts thereof.

6. The method according to claim 1, wherein the conditioner (K) further includes one or more polymers selected from the group consisting of Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquarternium-64, Polyquaternium-67, Polyquaternium-68, Polyquaternium-69, and Polyquaternium-86.

7. The method according to claim 1, wherein the conditioner (K) and/or the coloring agent (F) further includes at least one reducing agent selected from the group consisting of thiolactic acid, thioglycolic acid, cysteine, sodium sulfide, sodium sulfite, sodium thiosulfate, sodium dithionite, and the cosmetically acceptable salts thereof.

8. The method according to claim 1, wherein the straightening agent (G) includes at least one alkalizing agent selected from the group consisting of sodium hydroxide, potassium hydroxide, lithium hydroxide, and combinations thereof.

9. The method according to claim 1, wherein the straightening agent (G) is sodium hydroxide.

10. The method according to claim 1, wherein the straightening agent (G) includes at least one alkalizing agent selected from the group consisting of magnesium hydroxide, calcium hydroxide, and guanidinium hydroxide, and combinations thereof.

11. The method according to claim 1, wherein the at least one direct acid dye is present in an amount of from 0.4 to 1.8% by weight based on the total weight of the coloring agent (F).

12. The method according to claim 1, wherein the straightening agent (G) has a pH of from 11.5 to 13.0.

13. The method according to claim 1, wherein the conditioner (K) has a pH of from 3.5 to 5.5.

14. The method according to claim 1, wherein the coloring agent (F) has a pH of from 1.8 to 2.5.

15. The method according to claim 1, wherein, the straightening agent (G) includes less than 0.25% by weight of reducing agents selected from the group consisting of thiolactic acid, thioglycolic acid, cysteine, sodium sulfide, sodium sulfite, sodium thiosulfate, sodium dithionite, and the salts thereof.

16. The method according to claim 1, wherein the keratinous fibers include 0.9 or less than 1.3 moles of cysteic acid/100 mol of amino acid after straightening and dyeing as determined using FT-NIR spectroscopy.

* * * * *